(12) United States Patent  (10) Patent No.: US 7,438,694 B2
Boozer et al.  (45) Date of Patent: Oct. 21, 2008

(54) LANCING DEVICE

(75) Inventors: Brad Boozer, Marblehead, MA (US); Joseph Flaherty, Westford, MA (US); Timothy Golnik, Boxford, MA (US)

(73) Assignee: Agamatrix, Inc., Salem, NH (US)

( * ) Notice: Subject to any disclaimer, the term of this patent is extended or adjusted under 35 U.S.C. 154(b) by 85 days.

(21) Appl. No.: 11/276,598

(22) Filed: Mar. 7, 2006

(65) Prior Publication Data

US 2007/0213637 A1    Sep. 13, 2007

(51) Int. Cl.
*A61B 5/00* (2006.01)
*A61B 17/32* (2006.01)

(52) U.S. Cl. .................. 600/583; 606/181; 606/182; 600/584

(58) Field of Classification Search .............. 600/584, 600/583, 573; 606/181, 182, 183
See application file for complete search history.

(56) References Cited

U.S. PATENT DOCUMENTS

| 4,627,445 | A | 12/1986 | Garcia et al. |
| 4,995,402 | A | 2/1991 | Smith et al. |
| 5,820,551 | A | 10/1998 | Hill et al. |
| 6,053,930 | A | 4/2000 | Ruppert |
| 6,099,484 | A * | 8/2000 | Douglas et al. ............. 600/583 |
| 6,192,891 | B1 | 2/2001 | Gravel et al. |
| 6,197,257 | B1 | 3/2001 | Raskas |
| 6,210,420 | B1 | 4/2001 | Mauze et al. |
| 6,283,982 | B1 | 9/2001 | Levaughn et al. |
| 6,302,855 | B1 | 10/2001 | Lav et al. |
| 6,352,514 | B1 | 3/2002 | Douglas et al. |
| 6,379,317 | B1 | 4/2002 | Kintzig et al. |
| 6,479,618 | B1 | 11/2002 | Vonderhagen |
| 6,541,266 | B2 * | 4/2003 | Modzelewski et al. ........ 436/95 |
| 6,840,912 | B2 | 1/2005 | Kloepfer et al. |
| 6,852,119 | B1 | 2/2005 | Abulhaj et al. |
| 2005/0265094 | A1 | 12/2005 | Harding et al. |

FOREIGN PATENT DOCUMENTS

EP    1204371 B1 * 10/2004

\* cited by examiner

*Primary Examiner*—Max Hindenburg
*Assistant Examiner*—Michael C Stout
(74) *Attorney, Agent, or Firm*—Marina Larson & Associates, LLC

(57) ABSTRACT

A lancing device is used with a lancet for lancing body tissue to result in a wound for bleeding. An improved lancing device has a priming knob having a slanted priming notch rotatably connected to the lancing device about an axis of rotation generally parallel to a central axis of the lancing device and a strike path of a lancet carrier. Rotation, translation, or both rotation and translation of the priming knob allows a user to prime the lancing device.

11 Claims, 11 Drawing Sheets

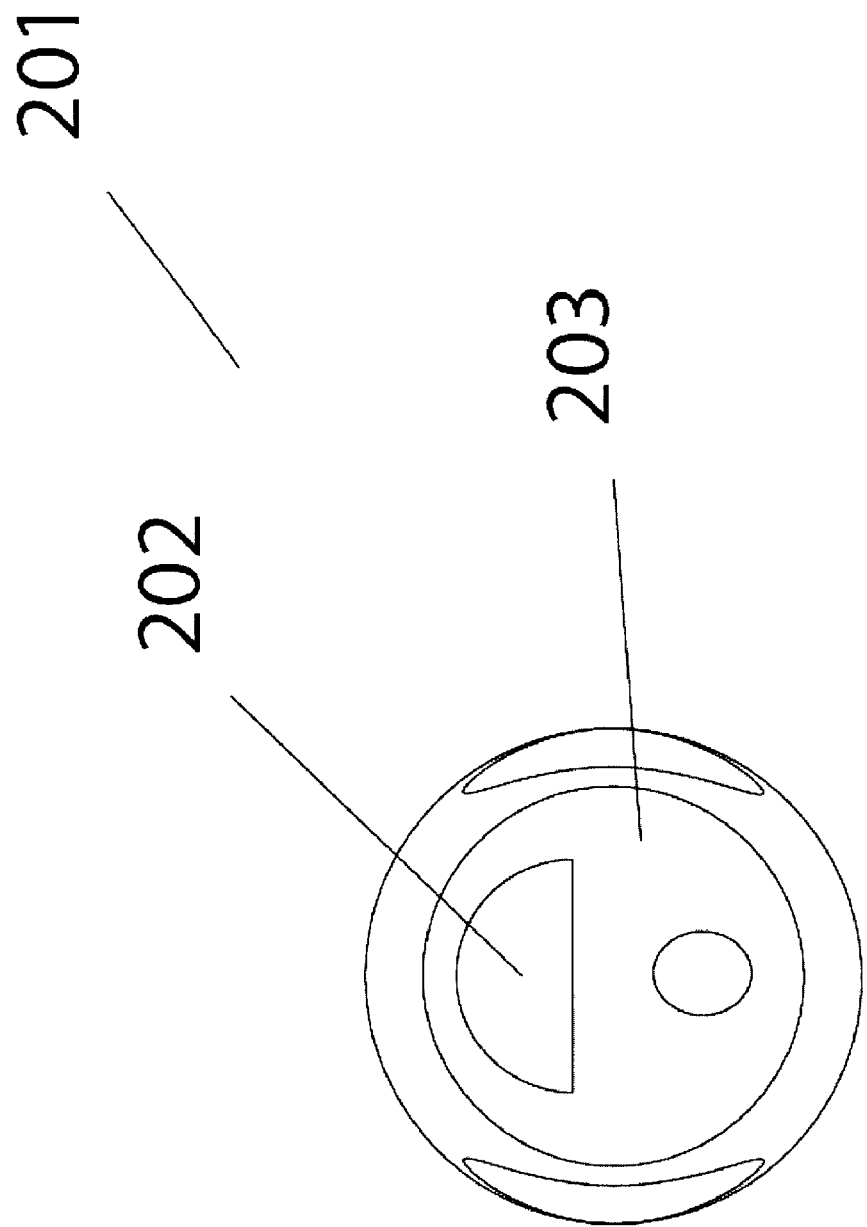

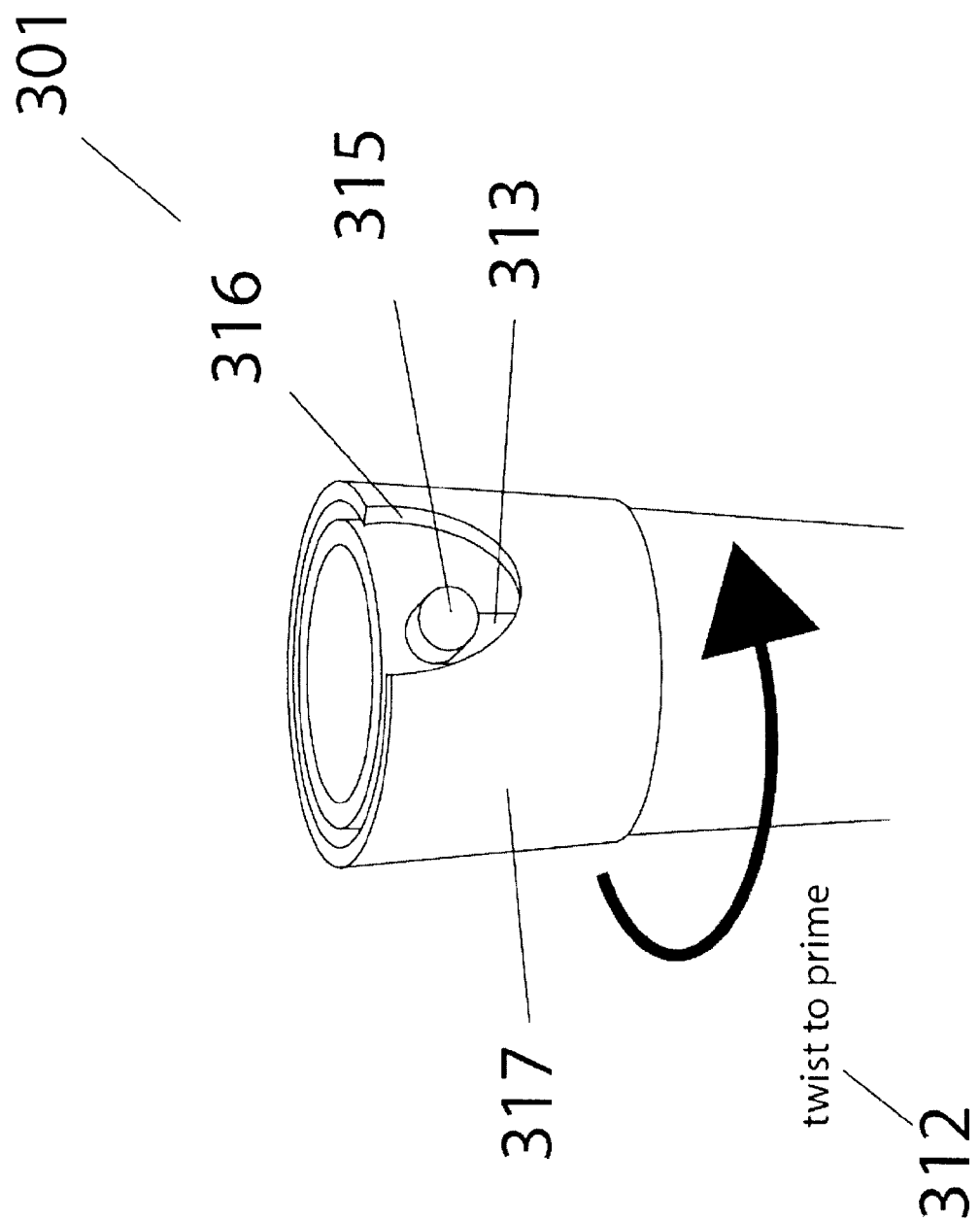

LANCING DEVICE

BACKGROUND

Lancing devices are typically used for the lancing of body tissue to result in a wound for bleeding. A blood sample then may be collected from the wound for measuring the concentration of an analyte such as glucose.

Currently available lancing devices, such as those disclosed in U.S. Pat. Nos. 6,053,930, 6,852,119, and 6,479,618 typically have a lancet carrier (including a lancet) and a spring loaded lancet driver mounted within a housing. On priming, the spring loaded lancet driver serves to store the energy required to propel the lancet carrier along the inside of the housing toward the skin of a user. The propulsion of the lancet causes the lancet to impact against and puncture the skin, causing a wound large enough for sampling blood. Such blood sampling is often painful and inconvenient.

Many users of such lancing devices suffer from physical impairments, such as arthritis, that prevent them from being able to adequately manipulate the priming means of the devices thereby failing to properly prime them. Such improper use of a lancet device often results in inadequate wound size for blood sampling and may require repeat lancing which causes more pain and multiple wounds. As a result, many patients may not be able to, or simply decide not to sample blood as frequently as suggested by their doctors in order to monitor their physiological functions adequately.

SUMMARY OF INVENTION

An improved lancing device is provided that is user-friendly and easy to use. The present invention provides a lancing device in which rotation, translation, or both rotation and translation of a priming knob allows a user to prime the device using whatever motion is easiest. In one embodiment, the lancing device has a priming knob having a slanted priming notch rotatably connected to the lancing device about an axis of rotation generally parallel to a central axis of the lancing device and a strike path of a lancet carrier.

DESCRIPTION OF DRAWING

FIG. 2A is a end view of the lancing end of a lancing device in accordance with an embodiment of the present invention.

FIG. 3 is an isometric view of a lancing device showing an embodiment of the present invention.

DETAILED DESCRIPTION OF INVENTION

Figure 1A:
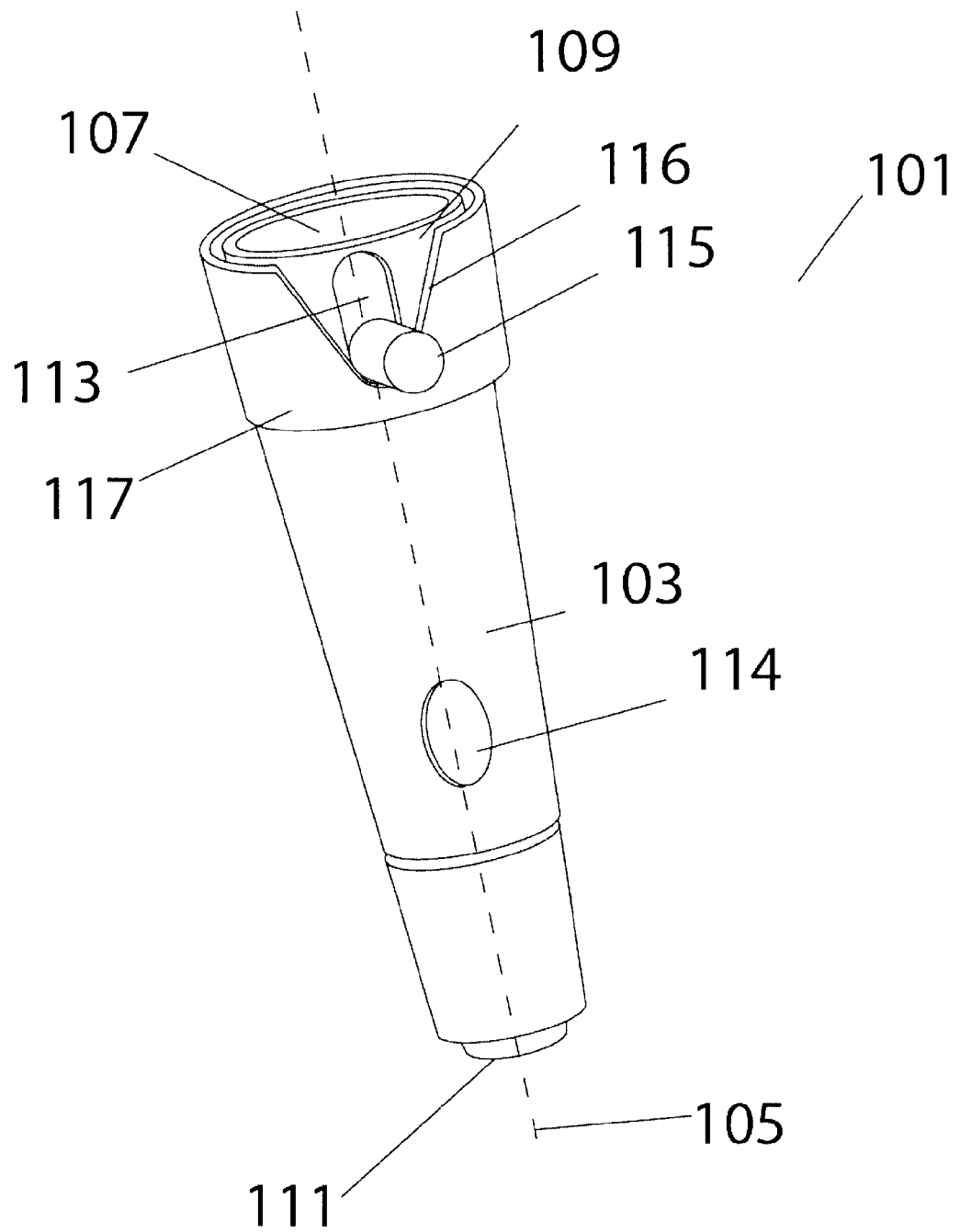
FIG. 1A is an isometric view of a lancing device in accordance with an embodiment of the present invention.

Lancing devices of the past including those disclosed in U.S. Pat. Nos. 6,053,930, 6,852,119, 6,479,618, and 6,210,420, all of which are herein incorporated by reference, typically have a lancet carrier (including a lancet) and a spring loaded lancet driver, mounted within a housing. As shown in FIG. 1B (FIG. 1 of U.S. Pat. No. 6,210,420) these lancet devices 1101 typically have a housing 1103 with an internal channel 1104, a lancet 1106 having a needle 1105 connected to a lancet carrier 1113, and a spring loaded lancet driver 1108 for driving the lancet carrier along the internal channel 1104 to the lancing end 1111 and bodily tissue 1112. The devices also have a priming means for priming the lancet device and storing energy in lancet driver 1108. In FIG. 1B the priming means is priming handle 1110. When a user pulls the handle 1110 away from the lancing end 1111 of device 1101, the lancet carrier 1113 is locked into a primed position where energy is stored in spring 1108 (i.e. the lancet driver). When a user presses release button 1114, the energy stored in spring 1108 is released as the lancet carrier is driven along the internal channel 1104 toward the bodily tissue 1112 of a user.

The present invention provides an improvement to the priming means of the lancing devices of the past. Instead of requiring a user to pull up on the priming handle 1110 of the past, priming may now also be accomplished by rotating, translating, or both rotating and translating, a priming knob that converts the rotational movement into translational movement (priming movement) of the lancet carrier. The improvement comprises a priming knob having a slanted priming notch rotatably connected to the lancing device about an axis of rotation generally parallel to a central axis of the device, wherein (i) rotation of the priming knob; (ii) movement of the priming knob along an axis generally parallel to the central axis of the device; or (iii) both rotation of the priming knob and movement of the priming knob along the axis generally parallel to the central axis of the device, primes a lancet driver and places the lancet carrier into the primed position, thereby priming the device.

A method for priming the improved lancing device of the present invention is also provided. The method comprises the steps of, by a user:

(i) inserting a lancet into a lancet carrier of a lancing device comprising the improvement described above, (ii) priming the lancing device by: rotating the priming knob of the lancing device; moving the priming knob along an axis generally parallel to the central axis of the housing; or both rotating the priming knob of the lancing device and moving the priming knob along an axis generally parallel to the central axis of the housing, (iii) placing the lancing end of the device next to the user's body tissue, and (iv) lancing the user's body tissue.

In a preferred embodiment, after a user performs step (ii) the lancet will be protected by the housing thereby allowing the user to perform step (iii) by placing the lancing end of the device directly against their body tissue (e.g. skin). After the lancing device is primed, the user may then perform step (iv) by pressing a release button that releases the lancet driver that drives the lancet carrier toward the user's body tissue.

The terms priming and primes the device as they are used herein are understood to mean that the lancet carrier is placed into a locked and primed position wherein energy is stored in the lancet driver that will be released upon activation of a lancet release. As demonstrated in FIGS. 1A and 1B the lancet release may be release button 114, 1114.

Figure 1B:
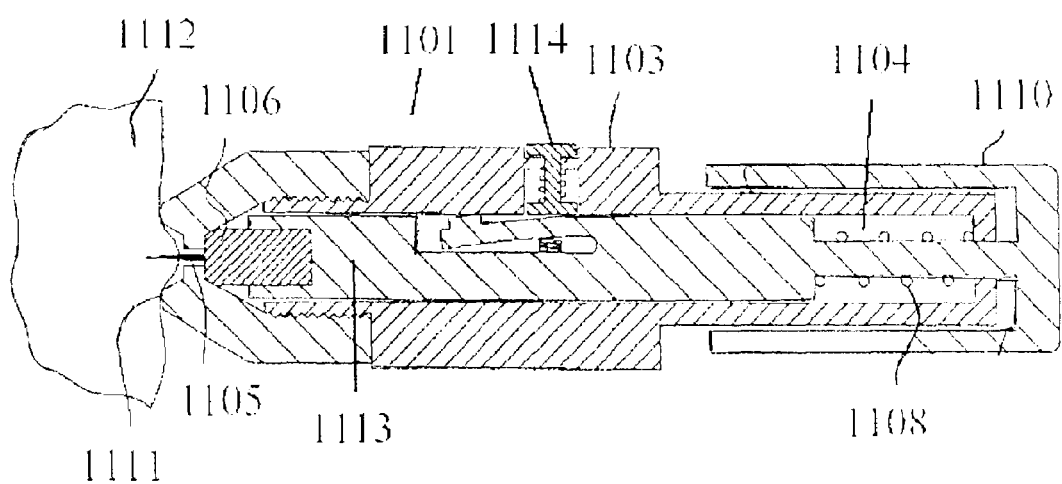
FIG. 1B is a cross-section side view of a prior art lancing device.

FIG. 1A shows a lancing device for lancing body tissue to result in a wound for bleeding in accordance with an embodiment of the present invention. Lancing device 101 comprises:

(1) a generally annular housing 103 having a central axis 105 and an internal channel 107 extending along the central axis 105 terminating at a priming end 109 of the housing 103 and at an opposed lancing end 111 of the housing 103;

(2) a priming knob 117 rotatably and translationally connected about the housing 103 to permit rotation about an axis of rotation generally parallel to the central axis 105 of the housing 103 and translation in a direction parallel to the axis of rotation, wherein the priming knob 117 comprises a slanted priming notch 116 for priming interaction with a priming protrusion 115 of a lancet carrier 113, (3) the lancet carrier 113 is translationally mounted within the internal channel of the housing 103 for carrying a lancet along a strike path that is generally parallel with the central axis 105, the strike path of the lancet carrier 113 starting from a primed position toward the priming end 109 of the housing 103 wherein the lancet is shielded by the housing 103 and ending at a lanced position wherein a tissue penetrating portion of the lancet extends outwardly from the lancing end 111 of the housing 103, the lancet carrier 113 comprising the priming protrusion 115 for priming interaction with the slanted priming notch 116 of the priming knob 117; and (4) a lancet carrier driver disposed within the internal channel 107 of the housing 103, the lancet carrier driver being operatively engaged with the lancet carrier 113 when driving the lancet carrier 113 along the strike path from the primed position to the lanced position;

wherein when the slanted priming notch 116 is in priming interaction with the priming protrusion 115 of the lancet carrier 113: (i) rotation of the priming knob 117; (ii) movement of the priming knob 117 along an axis generally parallel to the central axis 105 of the housing 103; or (iii) both rotation of the priming knob 117 and movement of the priming knob 117 along an axis of generally parallel to the central axis 105 of the housing 103, primes the lancet driver 113 and places the lancet carrier 113 into the primed position.

As shown in FIG. 1A, in a preferred embodiment the priming knob 117 is rotatably connected about the housing 103 at the priming end 109 of the housing 103. However, the priming knob may be disposed about the housing 103 anywhere along the housing 103, for example, at the lancing end 111 of the housing 103 or in the middle of the housing 103 between priming end 109 and lancing end 111 provided that it is in priming interaction with the device. As is further shown in FIG. 1A, the axis of rotation of the priming knob is preferably the central axis 105 of the housing 103. In another preferred embodiment the strike path of the lancet carrier is along the central axis 105 of the housing 103.

In a further embodiment a lancet and an analyte monitoring meter are combined in a single device having a priming knob described above. The combination allows for the reduction of the number of pieces of equipment required to perform an analyte measurement. For example U.S. Pat. Nos. 4,627,445, 6,192,891, and 6,840,912, all of which are herein incorporated by reference, disclose the combination of a analyte meter with a lancet in a single device. In the present embodiment the lancet housing described above provides mounting locations for a lancet assembly having the priming knob as well as analyte monitoring meter. The analyte monitoring meter is integrated into the housing and includes a display, a test strip interface, and a processor programmed to calculate and store the concentration of an analyte, preferably glucose, in a blood sample applied to a test strip. The housing has an opening for receiving the meter display as well as an opening for receiving a diagnostic test strip inserted into the test strip interface of the analyte monitoring meter. The display opening and test strip opening of the housing may be located anywhere along the housing, however, it is preferred that the display opening be on the side of the annular housing while the test strip opening be located at the lancing end of the housing. The analyte monitoring meter of the present invention is not limited. However, the analyte monitoring meter described in US patent publication number US 2005/0265094, herein incorporated by reference, is particularly preferred.

Figure 2B:
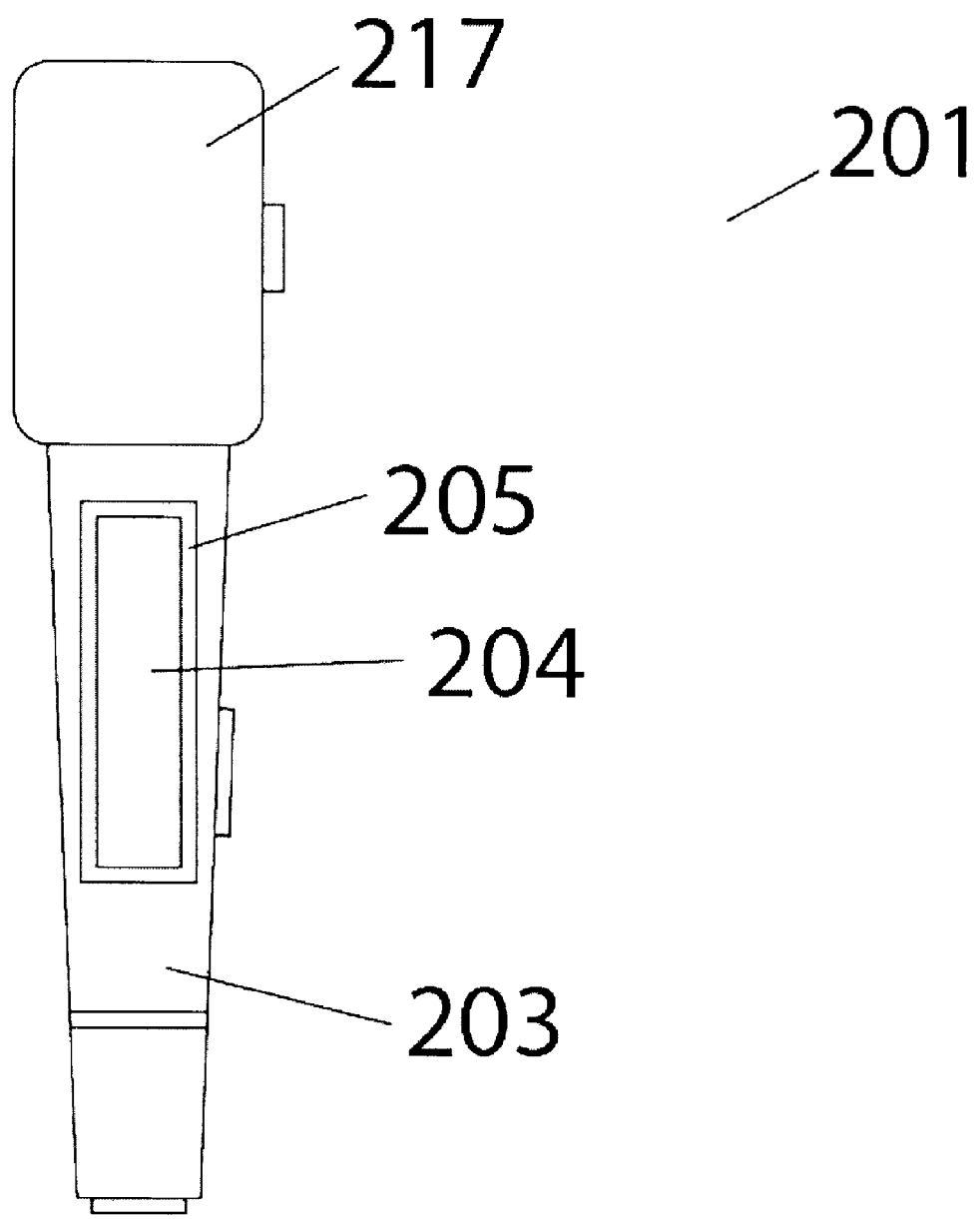
FIG. 2B is a side view of a lancing device in accordance with an embodiment of the present invention.

FIGS. 2A and 2B illustrate a combined lancet and analyte meter of the present invention having the priming knob 217 for priming the lancet portion the device. The housing 203 of the combined device 201 has a test strip opening 202 sized to receive a test strip and a display opening 205 sized to receive a meter display 204. In these figures device 201 has an analyte meter disposed within the generally annular housing 203. The analyte meter comprises a test strip interface for receiving a test strip; a processor programmed to perform a diagnostic test on a sample applied to a test strip received in the test strip interface to determine a concentration of an analyte within the sample; and the meter display 204 for displaying the result of the analyte measurement to the user. In preferred embodiments the processor is programed to determine the concentration of glucose within a blood sample.

The term "slanted priming notch" is herein defined as the area of interaction of the priming knob with a lancet carrier that allows conversion of rotational movement of the priming knob into translational movement and priming of the lancet carrier. In one embodiment, the slanted priming notch is smooth such that when the priming knob is rotated, the priming protrusion of the lancet carrier, will slide along the slanted priming notch.

Figure 2C:
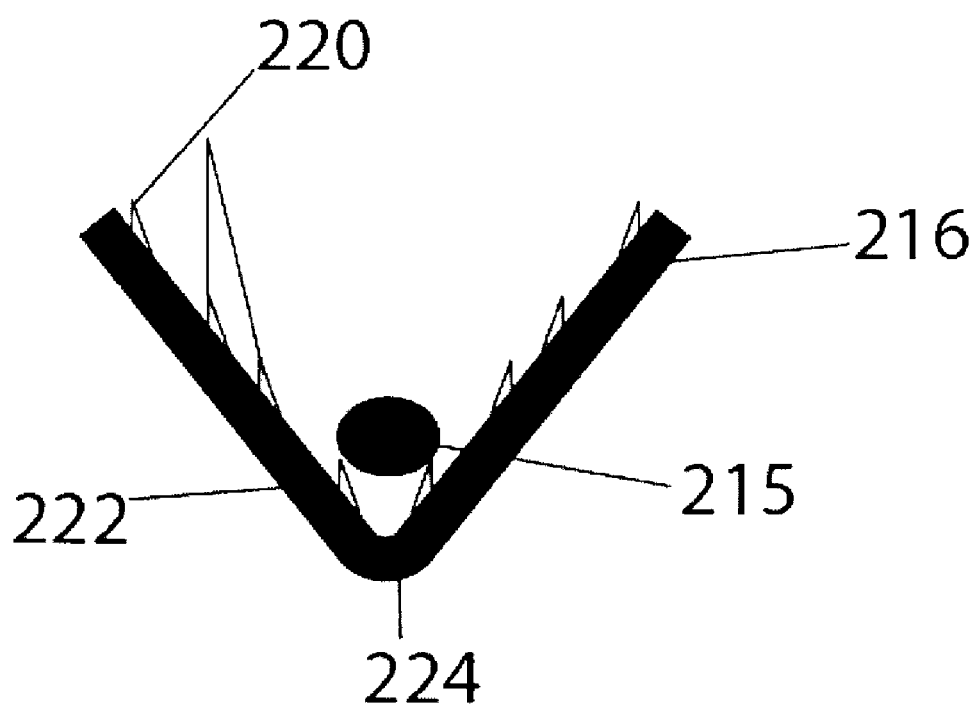
FIG. 2C is a side view of a priming knob in accordance with an embodiment of the present invention.

In another embodiment, and as shown in FIG. 2C, a slanted priming notch 216 comprises a series of teeth 220 that interact with a corresponding tooth 222, or teeth, on the priming protrusion 215 that prevent the priming protrusion from sliding to the bottom 224 of the notch 216 while priming of the device. The embodiment illustrated in FIG. 2C allows for a graduated step-wise ascent of the priming protrusion 215 along the priming notch 216 as a user rotates the priming knob.

In a preferred embodiment the slanted priming notch is symmetrically formed such that when the slanted priming notch is in priming interaction with the priming protrusion of the lancet carrier, clockwise rotation, counterclockwise rotation, or both clockwise and counterclockwise rotation of the priming knob primes the lancet driver and places the lancet carrier into a primed position. For example as detailed in FIG. 1A the slanted priming notch 116 is V-shaped wherein when the lancet carrier 113 is in a lanced position, the priming protrusion 115 rests at the bottom point of the V (as shown in FIG. 1A) and wherein when the priming knob 117 is rotated in either a clockwise or a counterclockwise direction by a user, the priming protrusion 115 slides up from the bottom point of the V along a slanted wall of the priming notch 116 until the device 101 is primed. Similarly, as shown in FIG. 3, the priming interaction of the priming protrusion 315 of the lancet carrier 313 may be with a symmetrical U-shaped priming notch 316 of a priming knob 317. As a user rotates 312 priming knob 317, in either a clockwise or counterclockwise direction (here in a counterclockwise direction), priming protrusion 315 slides up along the U-shaped wall of priming notch 316 until the lancet carrier 313 is placed in a primed position. By U-shaped it is herein understood to mean that the bottom of the notch is rounded (as compared to pointed in the case of a V-shaped priming notch) and that the walls of the notch are flared, with respect to the bottom of the notch, so that rotation of the priming knob primes the device.

Figure 4:
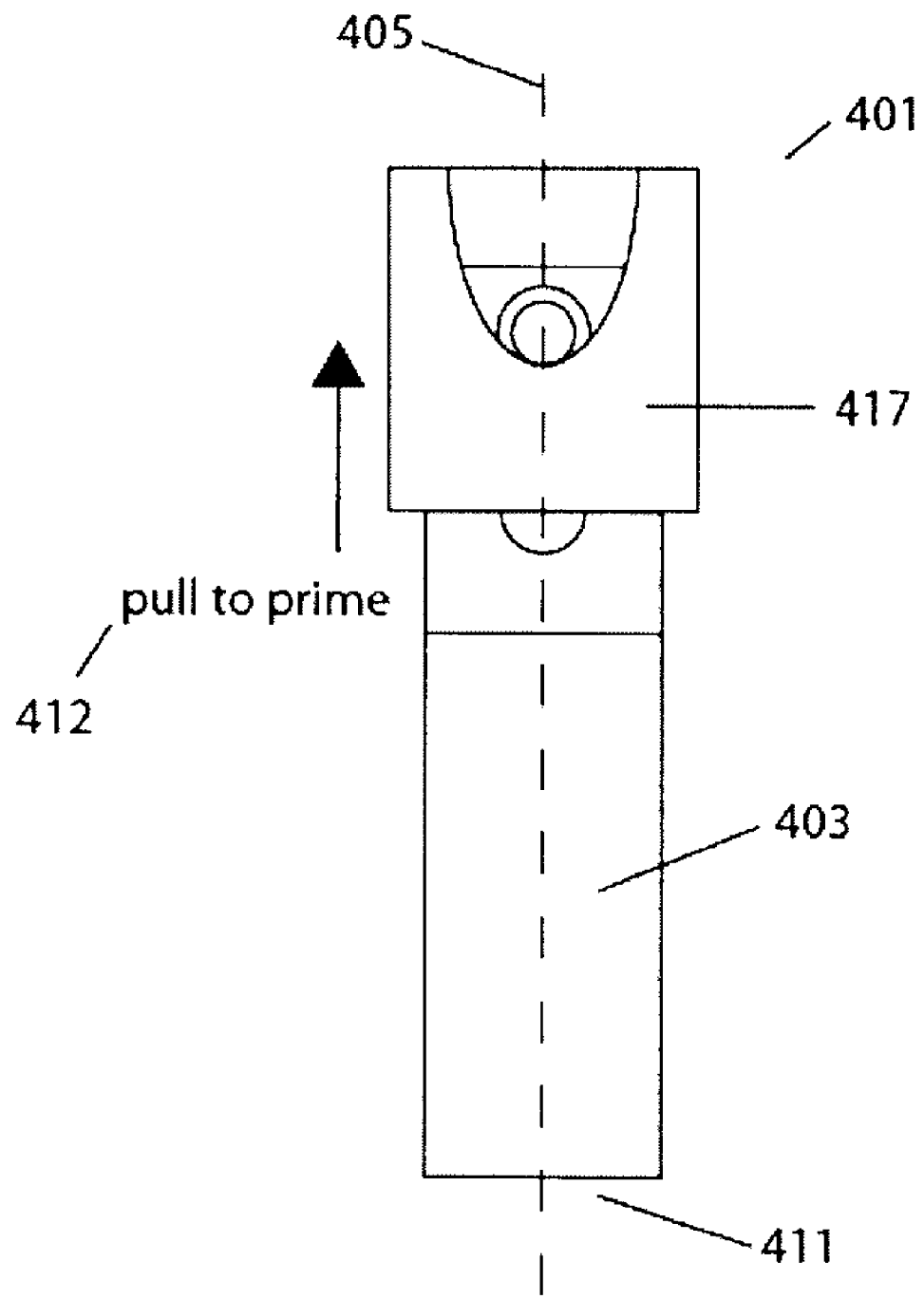
FIG. 4 is a side view of a lancing device showing an embodiment of the present invention.

In another mode of operation of the present invention, and as depicted in FIG. 4, in addition to rotating priming knob 417, a user may prime the lancet device 401 by moving 412 the priming knob 417 along an axis that is generally parallel to the central axis of the device. In FIG. 4, the device 401 may also be primed when the priming knob 417 is moved away from the lancing end 411 of the housing 403 along an axis generally parallel to the central axis 405 of the housing 403. Here the axis of movement of the priming knob 417 is along the central axis 405 of housing 403. It is also possible that a reverse priming mechanism be employed in the device. A reverse priming mechanism translates movement of the priming protrusion, the priming knob, or both, toward the lancing end of the device into priming movement of the lancet carrier by placing it into a primed position.

Figure 5:
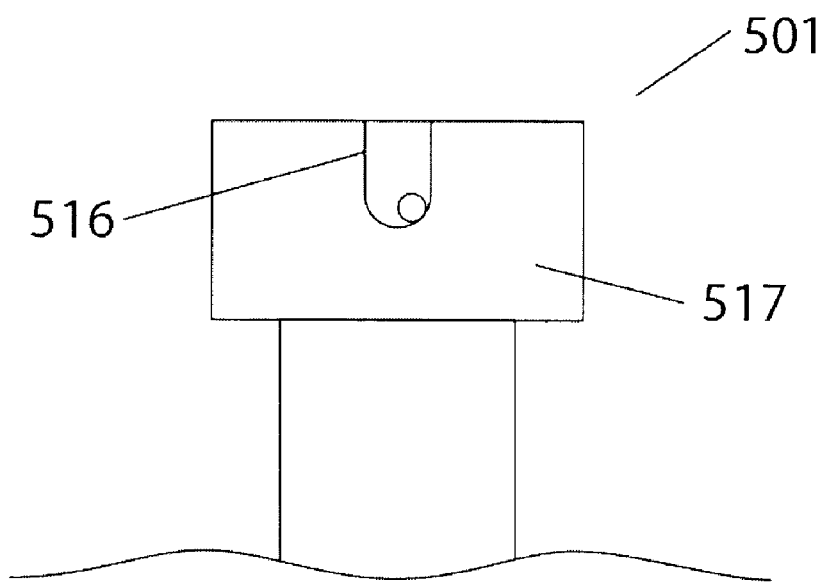
FIG. 5 is a front view of a lancing device showing an embodiment of the present invention.
Figure 6:
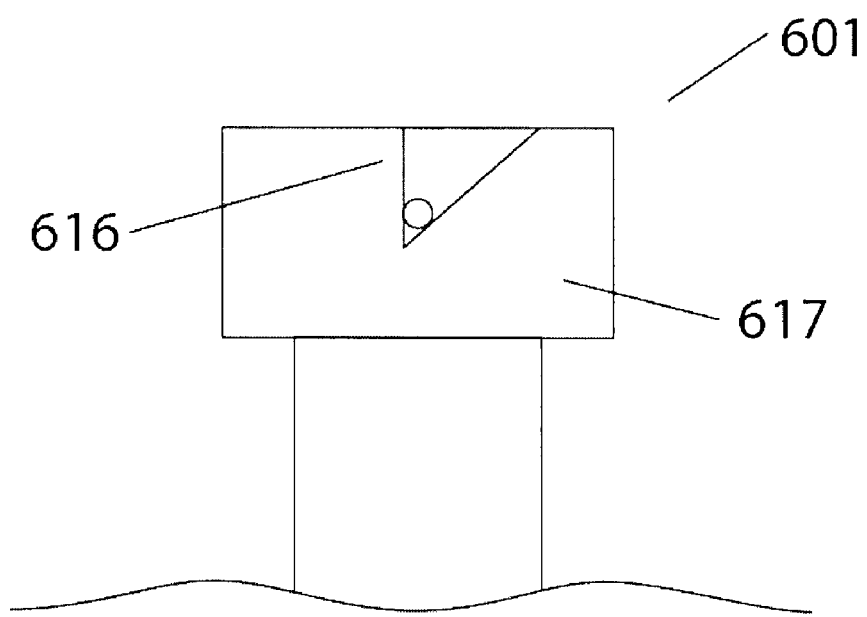
FIG. 6 is a front view of a lancing device showing an embodiment of the present invention.

Variations of the shape of the priming notch are herein contemplated and do not depart from the scope of the present invention so long as that when the priming notch is in priming interaction with the priming protrusion of the lancet carrier, clockwise rotation or counterclockwise rotation of the priming knob primes the lancet driver and places the lancet carrier into the primed position. The embodiments shown in FIGS. 1A and 3 detail preferred embodiments where the priming notch is symmetrical and where both clockwise and counterclockwise rotation of the priming knob 117, 317 may place the lancet carrier into the primed position thereby priming the lancet device 101, 301. In other embodiments the priming notch may be designed such that only rotating the priming knob in one direction primes the device. For example, as detailed in FIGS. 5 and 6, the priming notch 516, 616 may be designed such that it is not symmetrical and only clockwise (as depicted in FIG. 6) or only counterclockwise (as depicted in FIG. 5) rotation of the priming knob 517, 617 primes the device 501, 601.

Figure 7A:
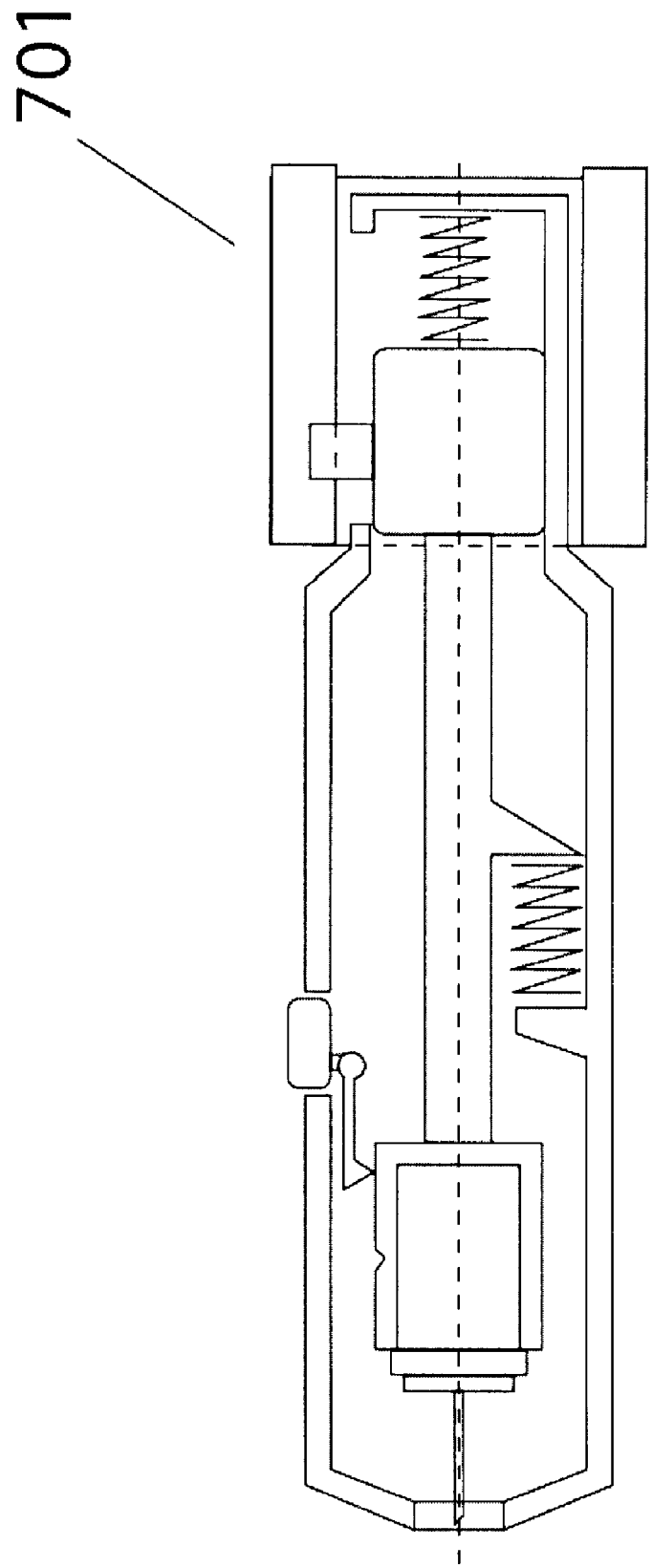
FIG. 7A is a side view of a lancing device showing an embodiment of the present invention.
Figure 7B:
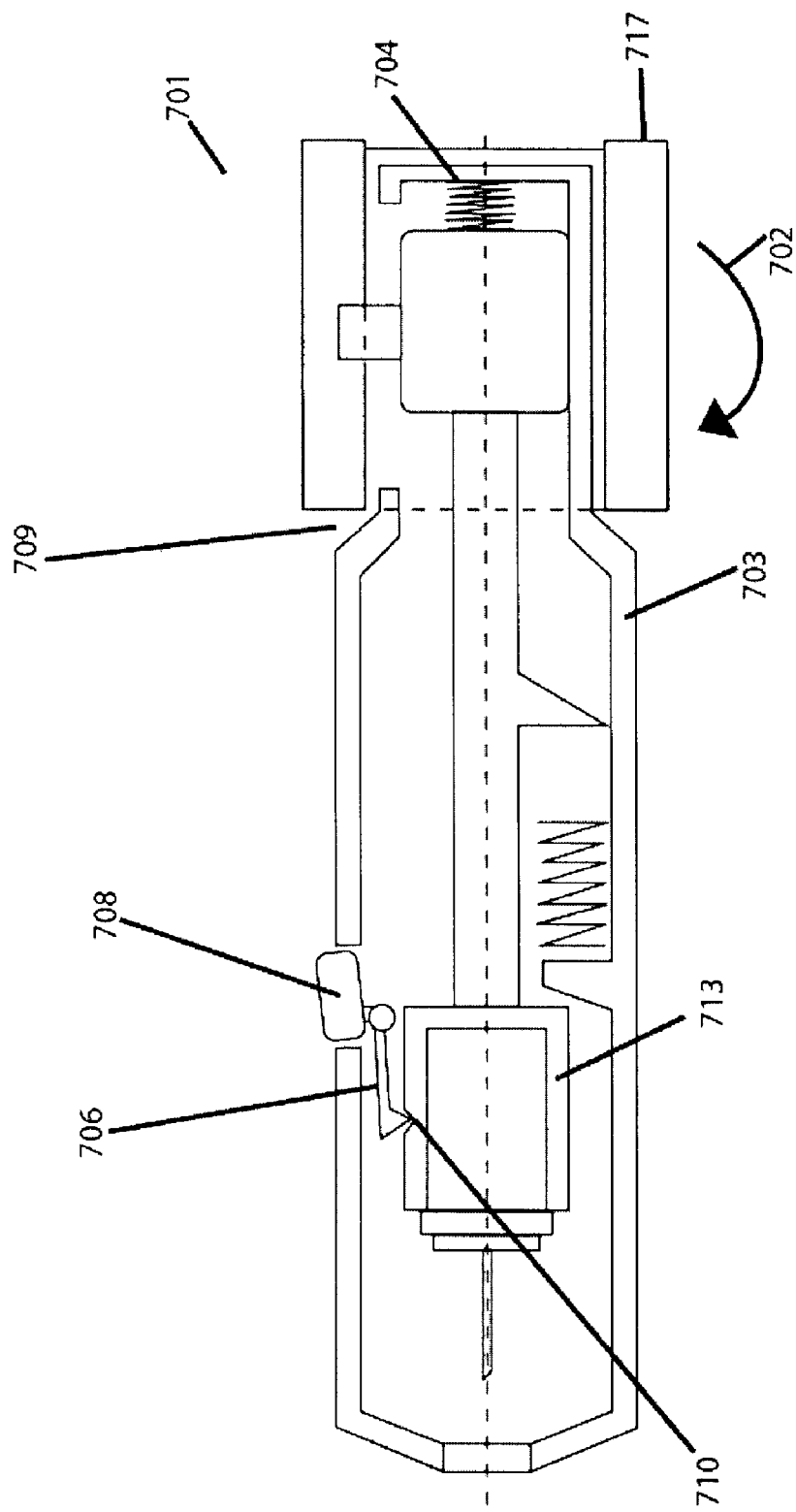
FIG. 7B is a side view of a lancing device showing an embodiment of the present invention.
Figure 7C:
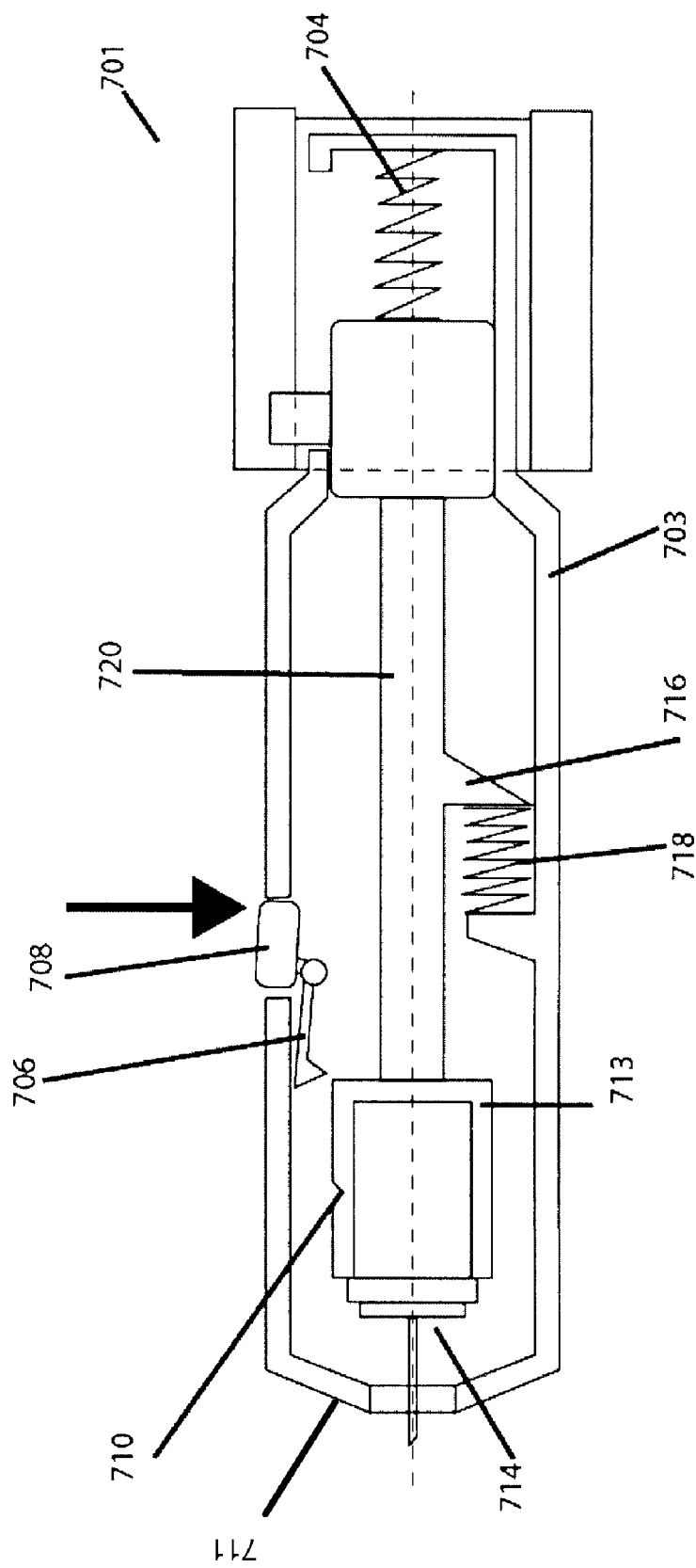
FIG. 7C is a side view of a lancing device showing an embodiment of the present invention.

FIGS. 7A, 7B, and 7C depict several cross sections of a preferred device in various configurations. In FIG. 7A, the device 701 has not yet been primed. In FIG. 7B, twisting 702 the priming knob 717 results in axially moving the lancing carrier 717 along the length of the device to compress a spring 704. Energy from twisting the knob 717 is stored in the spring 704 near the priming end 709 of the device 701. A hook 706 connected to the release button 708 engages the notch 710 in the lancing carrier 713 thereby priming the device 701. The device 701 is now ready to fire. FIG. 7C shows that pressing the release button 708 displaces the hook 706 and disengages it from the notch 710. This releases the energy stored in spring 704 and fires the lancet carrier 713 toward the lancing end 711 of housing 703. Upon firing, a lancet 714 carried in the lancet carrier 713 moves along the strike path, which is along the length of device 701, and lances bodily tissue. After the device 701 is fired the lancet carrier 713 retracts along the strike path. This retraction is possible because the wedge 716 attached to the stem 720 of the lancet carrier compressing the spring 718. The lancet carrier 713 eventually returns to its original configuration as illustrated in FIG. 7A.

Due to the ease and cost of manufacturing the lancing devices of the present invention, it is often preferred that the material of construction of the housing and the priming knob be thermoplastic resin. The priming notch of the priming knob, as well as the test strip and display openings of the housing, may be formed by a molding process or by a secondary process such as cutting the notch from the priming knob.

The invention claimed is:
1. A lancing device, for use with a lancet for lancing body tissue to result in a wound for bleeding, the lancing device comprising:
 (1) a generally annular housing having a central axis and an internal channel extending along the central_axis terminating at a priming end of the housing and at an opposed lancing end of the housing;
 (2) a priming knob rotatably and translationally connected about the housing to permit rotation about an axis of rotation generally parallel to the central axis of the housing and translation in a direction parallel to the axis of rotation, wherein the priming knob comprises a slanted priming notch for priming interaction with a priming protrusion of a lancet carrier,
 (3) a lancet carrier translationally mounted within the internal channel of the housing for carrying a lancet along a strike path that is generally parallel with the central axis, the strike path of the lancet carrier starting from a primed position toward the priming end of the housing wherein the lancet is shielded by the housing and ending at a lanced position wherein a tissue penetrating portion of the lancet extends outwardly from the lancing end of the housing, the lancet carrier comprising a priming protrusion for priming interaction with the slanted priming notch of the priming knob; and
 (4) a lancet carrier driver disposed within the internal channel of the housing, the lancet carrier driver being operatively engaged with the lancet carrier when driving the lancet carrier along the strike path from the primed position to the lanced position; wherein when the slanted priming notch is in priming interaction with the priming protrusion of the lancet carrier: (i) rotation of the priming knob is by itself sufficient to prime the lancet driver and places the lancet carrier into a primed position; (ii) movement of the priming knob along an axis generally parallel to the central axis of the housing is by itself sufficient to prime the lancet driver and places the lancet carrier into a primed position and (iii) a combination of both rotation of the priming knob and movement of the priming knob along an axis generally parallel to the central axis of the housing, prunes the lancet driver and places the lancet carrier into the primed position.

2. The device of claim 1, wherein the priming knob is rotatably connected to the housing at the priming end of the housing.

3. The device of claim 1, wherein the slanted priming notch is symmetrical such that when the priming notch is in priming interaction with the priming protrusion of the lancet carrier, clockwise rotation, counterclockwise rotation, or both clockwise and counterclockwise rotation of the priming knob primes the lancet driver and places the lancet carrier into the primed position.

4. The device of claim 1, wherein the slanted priming notch comprises a series of priming teeth and the priming protrusion comprises a priming tooth, and wherein when the slanted priming notch is in priming interaction with the priming protrusion of the lancet carrier and the priming knob is rotated, the priming tooth of the priming protrusion interacts with the priming teeth of the priming notch to provide a graduated ascent of the priming protrusion along the priming notch.

5. The device of claim 1, wherein:
 the housing has a test strip opening sized to receive a test strip and a display opening sized to receive a meter display,
 the device further comprising:

an analyte meter disposed within the generally annular housing, the analyte meter comprising: a test strip interface for receiving a test strip; a processor programmed to perform a diagnostic test on a sample applied to a test strip received in the test strip interface to determine a concentration of an analyte within the sample; and the meter display for displaying the result of the analyte measurement to the user.

6. The device of claim 5, wherein the processor is programmed to determine the amount of glucose in a sample.

7. A method for priming a lancing device, wherein the method comprises the steps of, by a user:
   (1) inserting a lancet into a lancet carrier of a lancing device comprising the improvement of:
   a priming knob, comprising a slanted priming notch, rotatably connected to the lancing device about an axis of rotation generally parallel to a central axis of the device, wherein (i) rotation of the priming knob is by itself sufficient to prime the lancet driver and places the lancet carrier into a primed position; (ii) movement of the priming knob along an axis generally parallel to the central axis of the device is by itself sufficient to prime the lancet driver and places the lancet carrier into a primed position and (iii) a combination of both rotation of the priming knob and movement of the priming knob along the axis generally parallel to the central axis of the device, primes a lancet driver and places the lancet carrier into a primed position,
   (2) priming the lancing device by: rotating the priming knob of the lancing device; moving the priming knob along an axis generally parallel to the central axis of the housing; or both rotating the priming knob of the lancing device and moving the priming knob along an axis generally parallel to the central axis of the housing,
   (3) placing the lancing end of the device next to the user's body tissue, and
   (4) lancing the user's body tissue.

8. The method of claim 7, wherein the slanted priming notch is symmetrical such that when a user performs the step of (ii) priming the lancing device, clockwise rotation, counterclockwise rotation, or both clockwise and counterclockwise rotation primes the lancet driver and places the lancet carrier into the primed position.

9. The method of claim 7, wherein the slanted priming notch comprises a series of priming teeth and the priming protrusion comprises a priming tooth, and wherein when the slanted priming notch is in priming interaction with the priming protrusion and the priming knob is rotated, the priming tooth of the priming protrusion interacts with the priming teeth of the priming notch to provide a graduated ascent of the priming protrusion along the priming notch.

10. In a lancing device, for use with a lancet carried by a lancet carrier, for lancing body tissue to result in a wound for bleeding, the improvement comprising:
    a priming knob, comprising a slanted priming notch, rotatably connected to the lancing device about an axis of rotation generally parallel to a central axis of the device, wherein (i) rotation of the priming knob is by itself sufficient to prime the lancet driver and places the lancet carrier into a primed position; (ii) movement of the priming knob along an axis generally parallel to the central axis of the device is by itself sufficient to prime the lancet driver and places the lancet carrier into a primed position; and (iii) a combination of both rotation of the priming knob and movement of the priming knob along the axis generally parallel to the central axis of the device, primes a lancet driver and places the lancet carrier into the primed position, thereby priming the device.

11. The device of claim 10, wherein the slanted priming notch comprises a series of priming teeth and the priming protrusion comprises a priming tooth, and wherein when the slanted priming notch is in priming interaction with the priming protrusion of the lancet carrier and the priming knob is rotated, the priming tooth of the priming protrusion interacts with the priming teeth of the priming notch to provide a graduated ascent of the priming protrusion along the priming notch.

* * * * *